(12) United States Patent
Chun et al.

(10) Patent No.: US 12,023,483 B2
(45) Date of Patent: Jul. 2, 2024

(54) ELECTRICAL STIMULATION DEVICE

(71) Applicant: KOREA UNIVERSITY RESEARCH AND BUSINESS FOUNDATION, Seoul (KR)

(72) Inventors: Hoon Jai Chun, Seoul (KR); Bo Ra Keum, Seoul (KR); Eun Sun Kim, Seoul (KR); Hyuk Soon Choi, Seoul (KR); Seung Han Kim, Seoul (KR); Jae Min Lee, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 136 days.

(21) Appl. No.: 17/609,388

(22) PCT Filed: Mar. 19, 2020

(86) PCT No.: PCT/KR2020/095046
§ 371 (c)(1),
(2) Date: Nov. 7, 2021

(87) PCT Pub. No.: WO2020/226474
PCT Pub. Date: Nov. 12, 2020

(65) Prior Publication Data
US 2022/0218984 A1 Jul. 14, 2022

(30) Foreign Application Priority Data
May 7, 2019 (KR) .......................... 10-2019-0053286

(51) Int. Cl.
*A61N 1/08* (2006.01)
*A61N 1/05* (2006.01)
*A61N 1/36* (2006.01)

(52) U.S. Cl.
CPC ............. *A61N 1/0509* (2013.01); *A61N 1/08* (2013.01); *A61N 1/36007* (2013.01)

(58) Field of Classification Search
CPC .. A61N 1/0507; A61N 1/0509; A61N 1/0517; A61N 1/08; A61N 1/36007;
(Continued)

(56) References Cited

U.S. PATENT DOCUMENTS

| | | | |
|---|---|---|---|
| 2001/0001819 A1 | 5/2001 | Lee et al. | |
| 2006/0106281 A1* | 5/2006 | Boulais | A61B 1/00059 600/101 |

(Continued)

FOREIGN PATENT DOCUMENTS

| | | |
|---|---|---|
| JP | 2004532700 A | 10/2004 |
| JP | 2009519050 A | 5/2009 |

(Continued)

OTHER PUBLICATIONS

International Search Report and Written Opinion for International Application PCT/KR2020/095046, filed Mar. 19, 2020, search report, dated Sep. 10, 2020.

(Continued)

*Primary Examiner* — Ankit D Tejani
*Assistant Examiner* — Joshua Brendon Solomon
(74) *Attorney, Agent, or Firm* — BOND, SCHOENECK & KING, PLLC; George R. McGuire (57) ABSTRACT

An electrical stimulation device according to an embodiment includes: an elongated element having working channels; a plurality of electrical stimulators each including a longitudinal member extending along the longitudinal direction of the working channel, and a tip which is installed at the distal end of the longitudinal member and configured to apply electrical stimulation to a subject; and a control unit that independently controls the plurality of electrical stimu- (Continued)

lators to vary the range of electric stimulation applied to the subject.

7 Claims, 7 Drawing Sheets

(58) Field of Classification Search
CPC .............. A61B 18/1492; A61B 1/2736; A61B 2018/00488; A61B 2018/00494; A61B 2018/143; A61B 2018/1475; A61B 2218/007
See application file for complete search history.

(56) References Cited

U.S. PATENT DOCUMENTS

| | | |
|---|---|---|
| 2010/0298761 A1 | 11/2010 | Staal |
| 2013/0231646 A1 | 9/2013 | Noar |
| 2016/0015451 A1 | 1/2016 | Shikhman |

FOREIGN PATENT DOCUMENTS

| | | |
|---|---|---|
| KR | 1020120140639 A | 12/2012 |
| KR | 20180023966 A | 3/2018 |
| KR | 1020190027342 A | 3/2019 |

OTHER PUBLICATIONS

Supplementary European Search Report of PCT/KR2020/095046, filed Mar. 19, 2020, dated Dec. 14, 2022. pp. 1-7.

* cited by examiner

ELECTRICAL STIMULATION DEVICE

CROSS REFERENCE TO RELATED APPLICATIONS

This is a National Stage Application filed under 35 U.S.C. 371 based on International Patent Application No. PCT/KR2020/095046, filed on Mar. 19, 2020, which claims priority to Korean Patent Application 10-2019-0053286 filed May 7, 2019. The entire disclosures of each of the foregoing are hereby incorporated herein by reference in their entireties.

TECHNICAL FIELD

Example embodiments relate to an electrical stimulation device.

BACKGROUND ART

A functional gastrointestinal disorder among gastrointestinal disorders is a chronic or relapsing disorder developed in approximately 40% of adults. Currently, various attempts including, for example, medication, endoscopic procedures, and surgical operations, are being made to treat the functional gastrointestinal disorder and metabolic obesity. However, such methods may not have significant effects, and may cost patients a lot and invite complications. Accordingly, an electrical gastrointestinal stimulation technology is being developed as a technology for treating a functional gastrointestinal disorder or disease. For example, Korean Patent Publication No. 10-2018-0023966 discloses "Devices for Gastrointestinal Stimulation and Uses Thereof."

DISCLOSURE OF THE INVENTION

Technical Goals

An aspect provides an electrical stimulation device that is used along with an endoscope and noninvasively applies electrical stimulation to a desired portion on a surface of a target.

Technical Solutions

According to an example embodiment, there is provided an electrical stimulation device including an elongated element having a working channel, a plurality of electrical stimulators including respective longitudinal members each extending in a longitudinal direction of the working channel and respective tips each provided at a distal end of the longitudinal members and configured to apply electrical stimulation to a target, and a controller configured to independently control the electrical stimulators to vary a range of electrical simulation to be applied to the target.

The controller may independently control a deployment or a withdrawal of the longitudinal members in the longitudinal direction of the working channel such that a space between the tips is adjusted.

The controller may control the longitudinal members to have a first configuration in which all of at least a portion of the longitudinal members withdraw into the working channel to contract and have a second configuration in which all of at least a portion of the longitudinal members deploy outside the working channel to expand.

The controller may control the longitudinal members to deploy in the longitudinal direction of the working channel until all the tips come into contact with a surface of the target.

The controller may apply different potentials to at least two of the tips.

The controller may control a movement of the elongated element along an inner cavity of the target, and control the longitudinal members such that the tips are not exposed to the inner cavity of the target from the working channel during the movement of the elongated element along the inner cavity of the target.

The elongated element may include an opening through which the longitudinal members pass, and a closely attached portion configured to surround the opening and configured to be closely attached to the surface of the target.

When the closely attached portion is closely attached to the surface of the target, the controller may suck air into the working channel through the opening.

Effects

According to example embodiments described herein, an electrical stimulation device may be used together with an endoscope and noninvasively apply electrical stimulation to a desired portion on a surface of a target.

The effects of the electrical stimulation device are not limited to what has been described above, and other additional aspects of example embodiments will be set forth in part in the description which follows and, in part, will be apparent from the description, or may be learned by practice of the disclosure.

BEST MODE FOR CARRYING OUT THE INVENTION

Hereinafter, some example embodiments will be described in detail with reference to the accompanying drawings. However, various alterations and modifications may be made to the example embodiments. The example embodiments are not construed as limited to the disclosure and should be understood to include all changes, equivalents, and replacements within the idea and the technical scope of the disclosure.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

In addition, terms such as first, second, A, B, (a), (b), and the like may be used herein to describe components. Each of these terminologies is not used to define an essence, order, or sequence of a corresponding component but used merely to distinguish the corresponding component from other component(s).

It should be noted that if it is described in the specification that one component is "connected," "coupled," or "joined" to another component, a third component may be "connected," "coupled," and "joined" between the first and second components, although the first component may be directly connected, coupled or joined to the second component.

Unless otherwise defined, all terms used herein including technical or scientific terms have the same meanings as those generally understood consistent with and after an understanding of the present disclosure. Terms, such as those defined in commonly used dictionaries, should be construed to have meanings matching with contextual meanings in the relevant art and the present disclosure, and are not to be construed as an ideal or excessively formal meaning unless otherwise defined herein.

Hereinafter, the example embodiments will be described in detail with reference to the accompanying drawings. When describing the example embodiments with reference to the accompanying drawings, like reference numerals refer to like components and a repeated description related thereto will be omitted for increased clarity and conciseness.

Figure 1:
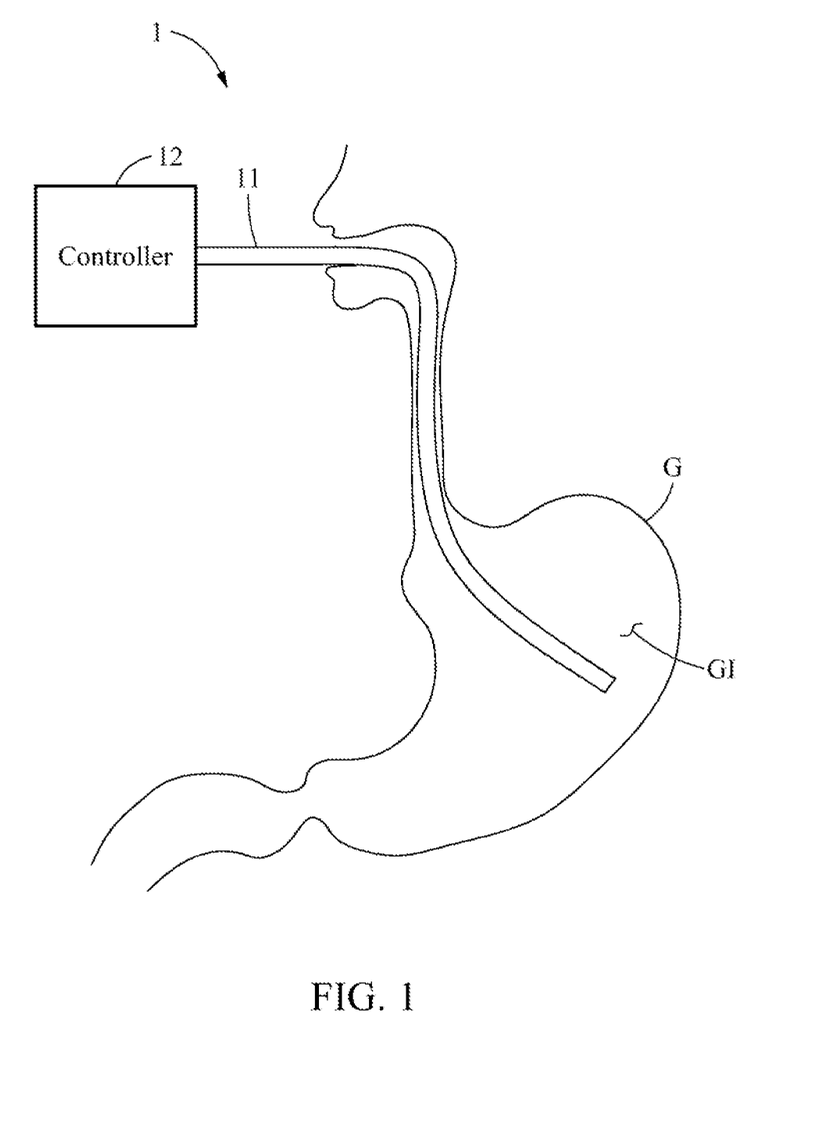
FIG. 1 illustrates a schematic structure of an electrical stimulation device according to an example embodiment.
Figure 2:
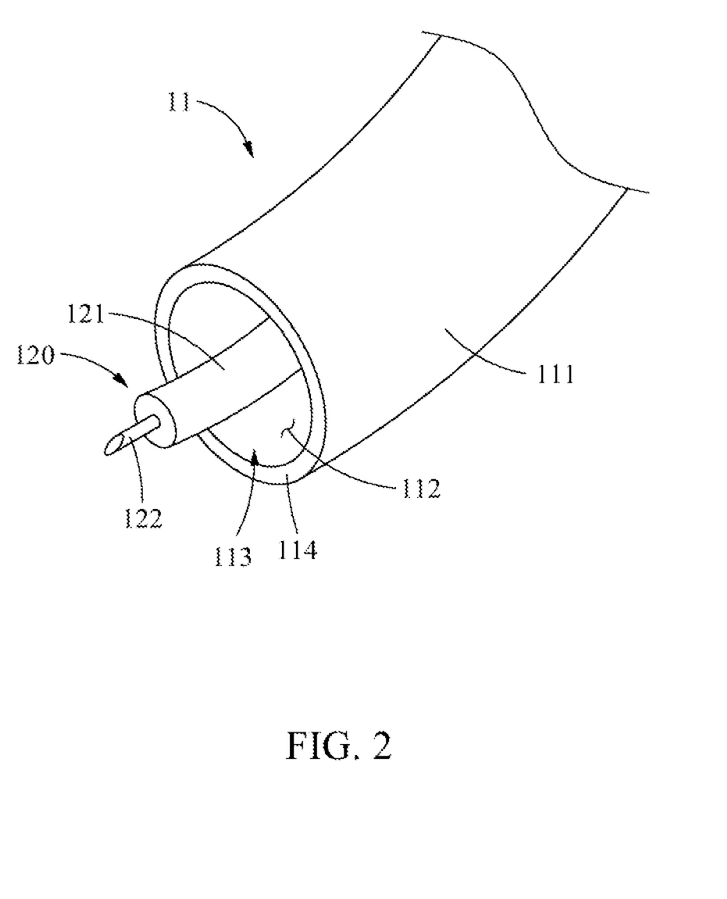
FIG. 2 is a perspective view of an end structure of an elongated element of an electrical stimulation device according to an example embodiment.

FIG. 1 illustrates a schematic structure of an electrical stimulation device according to an example embodiment. FIG. 2 is a perspective view of an end structure of an elongated element of an electrical stimulation device according to an example embodiment.

Referring to FIGS. 1 and 2, according to an example embodiment, an electrical stimulation device 1 may be noninvasively inserted into an inner cavity of a target to apply electrical stimulation to the target. The target described herein may include a living creature, such as, for example, a human and an animal. The electrical stimulation device 1 may include a catheter 11 and a controller 12 configured to control the catheter 11. The catheter 11 may be inserted into an oral cavity of the target and move along an esophagus, and an end thereof may then be positioned in a gastrointestinal tract GI of the stomach and intestines G. The catheter 11 may apply electrical stimulation to the surface of the gastrointestinal tract GI.

The catheter 11 may include an elongated element 111 and an electrical stimulator 120.

The elongated element 111 may be inserted into the gastrointestinal tract GI while moving along the inner cavity of the target. The elongated element 111 may be provided in a form of a tube. The elongated element 111 may have a material suitable to be bent such that an end portion thereof readily approaches a desired portion. For example, the elongated element 111 may be formed of a silicon material. Also, the elongated element 111 may be formed of a water-resistant material. For example, the elongated element 111 may include titanium. The elongated element 111 may have a length suitable for the end portion thereof to reach the gastrointestinal tract GI from the oral cavity of the target.

The elongated element 111 may have a working channel 112. The working channel 112 may be formed inside the elongated element 111 along a longitudinal direction of the elongated element 111. Thus, the elongated element 111 may be hollow inside.

The elongated element 111 may include an opening 113 and a closely attached portion 114.

The opening 113 may be configured to communicate with the working channel 112. The opening 113 may allow entry and exit of the electrical stimulator 120 from the inside of the working channel 112 to the outside of the working channel 112 or from the outside of the working channel 112 to the inside of the working channel 112. The opening 113 may be formed at a distal end of the elongated element 111. The opening 113 may have a size suitable for the entry and exit of the electrical stimulator 120 to and from the outside or inside of the working channel 112. The opening 113 may be formed in a circle, but not limited thereto.

The opening 113 may include an opening and closing element that selectively allows the entry or exit of the electrical stimulator 120. For example, the opening and closing element may be provided in a structure of a plate membrane that covers at least a portion of the opening 113.

The closely attached portion 114 may be configured to be closely attached to the surface of the inner cavity of the target. The closely attached portion 114 may be formed at an end of the elongated element 111 to surround the opening 113. When the closely attached portion 114 is attached to the surface of the inner cavity of the target, a suction force of a predetermined pressure may act through the opening 113, and accordingly, close contact between the closely attached portion 114 and the surface of the inner cavity of the target may be maintained.

The electrical stimulator 120 may apply electrical stimulation to a desired portion on the surface of the inner cavity of the target. The electrical stimulator 120 may be disposed in the working channel 112 formed inside the elongated element 111, and move along the working channel 112.

The electrical stimulator 120 may include a longitudinal member 121 and a tip 122.

The longitudinal member 121 may deploy or withdraw along the working channel 112. The longitudinal member 121 may deploy or withdraw while passing through the opening 113 formed at the distal end of the working channel 112. The longitudinal member 121 may extend in a longitudinal direction of the working channel 112. The longitudinal member 121 may include an electrical lead that transfers electrical stimulation to the surface of the inner cavity of the target. The electrical lead may extend along the longitudinal member 121 to be connected to a controller 12 outside a body.

The tip 122 may apply electrical stimulation to the surface of the inner cavity of the target. The tip 122 may be provided at a distal end of the longitudinal member 121. The tip 122 may be provided in an elongated form extending from the distal end of the longitudinal member 121, but not limited thereto. A distal end of the tip 122 may be formed not to bore through the surface of the inner cavity of the target but to effectively transfer electrical stimulation to the surface of the inner cavity of the target. The tip 122 may include a conductive material through which electricity flows stably. In addition, the tip 122 may include an acid-resistant material. In such a case, the acid-resistant material may be coated on an outer surface of the tip 122.

The controller 12 may control the catheter 11. For example, the controller 12 may control a movement of the elongated element 111 along the inner cavity of the target. Alternatively, the elongated element 111 may be controlled by a user's manipulation.

The controller 12 may control a deployment or withdrawal of the longitudinal member 121 along the working channel 112. When the longitudinal member 121 deploys or withdraws, the controller 12 may determine a degree of exposure of at least a portion of the longitudinal member 121 and the tip 122 to the outside of the working channel 112. The controller 12 may control the longitudinal member 121 not to deploy until the closely attached portion 114 is attached to the surface of the inner cavity of the target. The controller 12 may control the longitudinal member 121 to deploy until the tip 122 comes into contact with the surface of the inner cavity of the target.

The controller 12 may determine an orientation of the electrical stimulator 120. In this case, the controller 12 may determine an orientation of at least a portion of the longitudinal member 121 to allow the portion of the longitudinal member 121 to be bent such that the tip 122 faces toward the surface of the inner cavity of the target. For example, the longitudinal member 121 may be bent to have at least two bent portions. As the orientation of the longitudinal member 121 is controlled as described above, electrical stimulation may be applied to a desired portion on the surface of the inner cavity of the target.

The controller 12 may control electrical energy to be applied by the tip 122 to the surface of the inner cavity of the target. The electrical energy may be determined by a voltage, a current, a frequency, an amplitude, a duty cycle, or the like. In addition, the controller 12 may vary the electrical energy to be applied by the tip 122.

The controller 12 may generate a suction force from the outside of the working channel 112 to the inside of the working channel 112 through the opening 113. For example, when the closely attached portion 114 is attached to the surface of the inner cavity of the target, the controller 12 may allow air to be sucked into the inside of the working channel 113 through the opening 113 to maintain close contact between the closely attached portion 114 and the surface of the inner cavity of the target.

Figure 3:
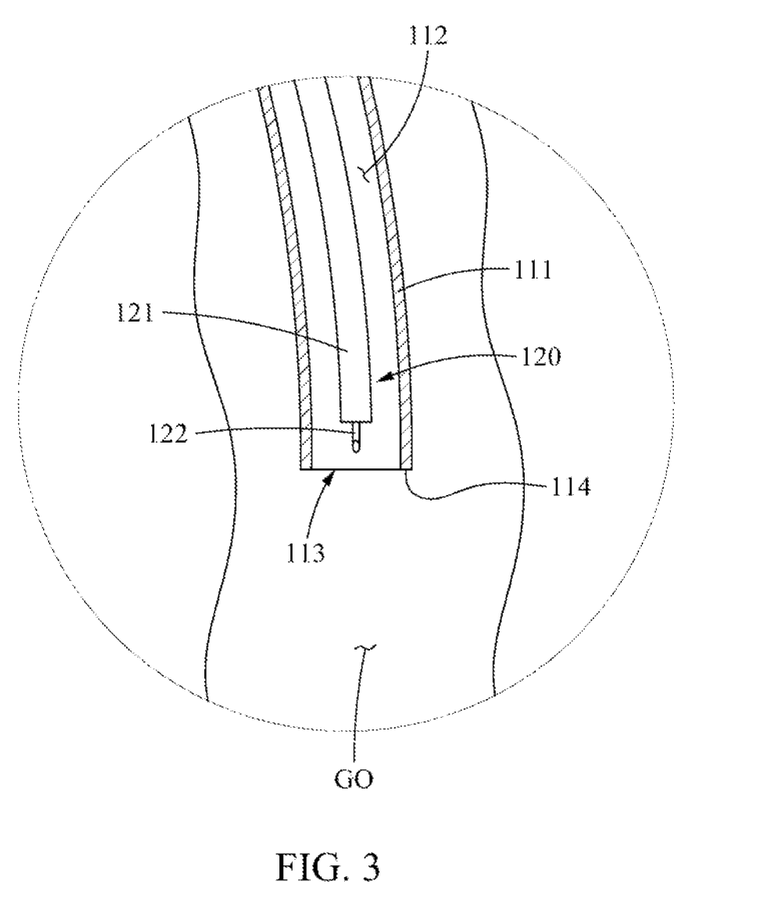
FIG. 3 illustrates a movement of an elongated element of an electrical stimulation device along a gastrointestinal tract according to an example embodiment.

FIG. 3 illustrates a movement of an elongated element of an electrical stimulation device along a gastrointestinal tract according to an example embodiment.

Referring to FIG. 3, the elongated element 111 may be controlled (by the controller 12 of FIG. 1) to move along the esophagus (indicated by GO) of the target. In this case, the longitudinal member 121 and the tip 122 of the electrical stimulator 120 may be controlled (by the controller 12 of FIG. 1) to be disposed inside the working channel 112 and not to be exposed to the outside of the working channel 112 through the opening 113. This may prevent the tip 122 from damaging a tissue of the target while the elongated element 111 is reaching a desired portion on the surface of the inner cavity of the target.

Figure 4:
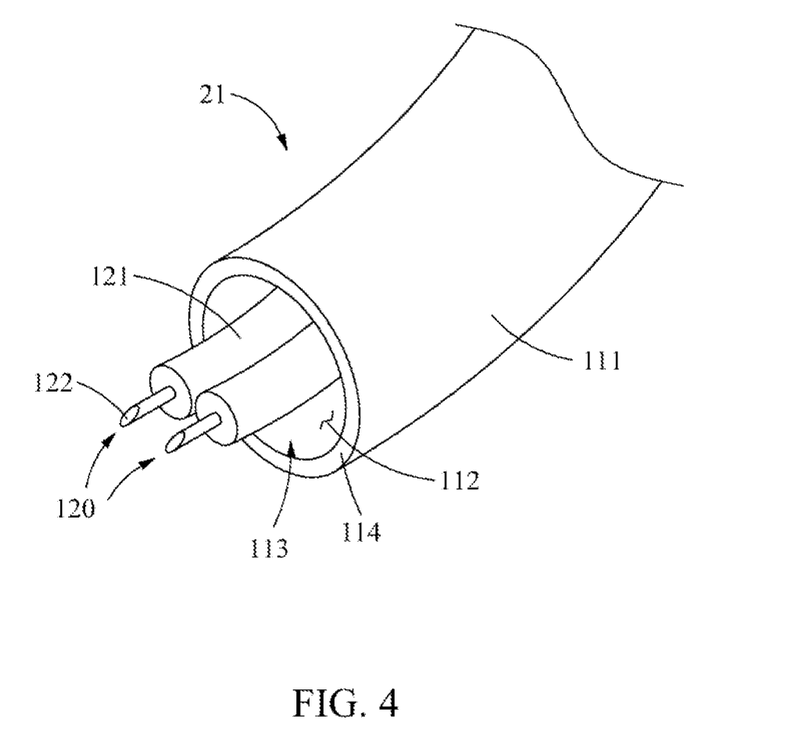
FIG. 4 is a perspective view of a first configuration of an electrical stimulation device according to another example embodiment.
Figure 5:
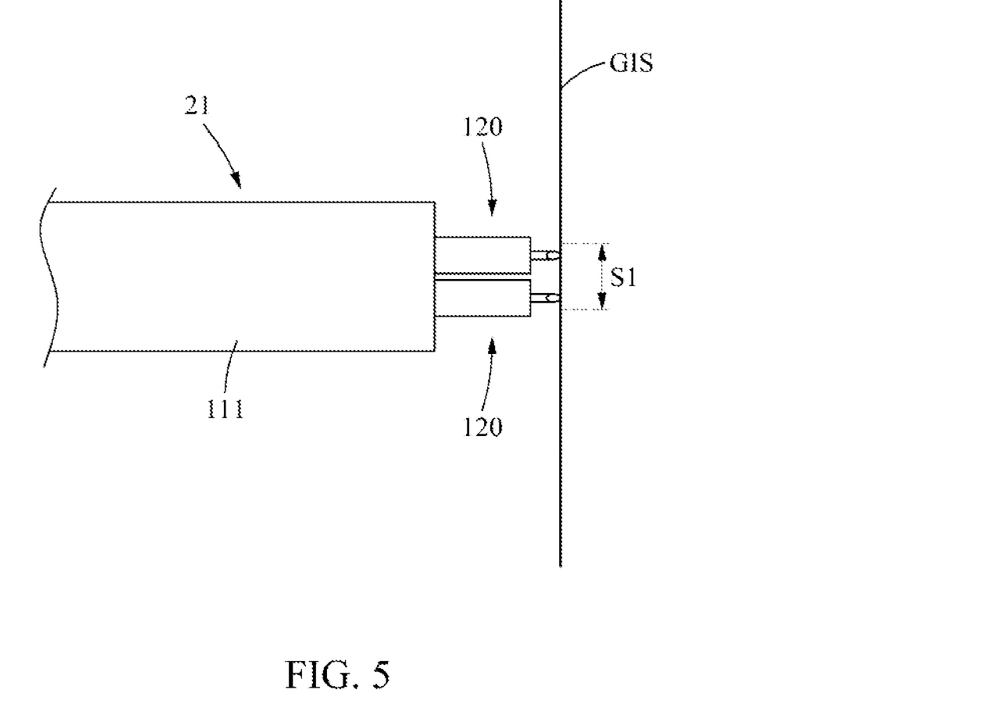
FIG. 5 illustrates a first configuration of a plurality of electrical stimulators of FIG. 4.
Figure 6:
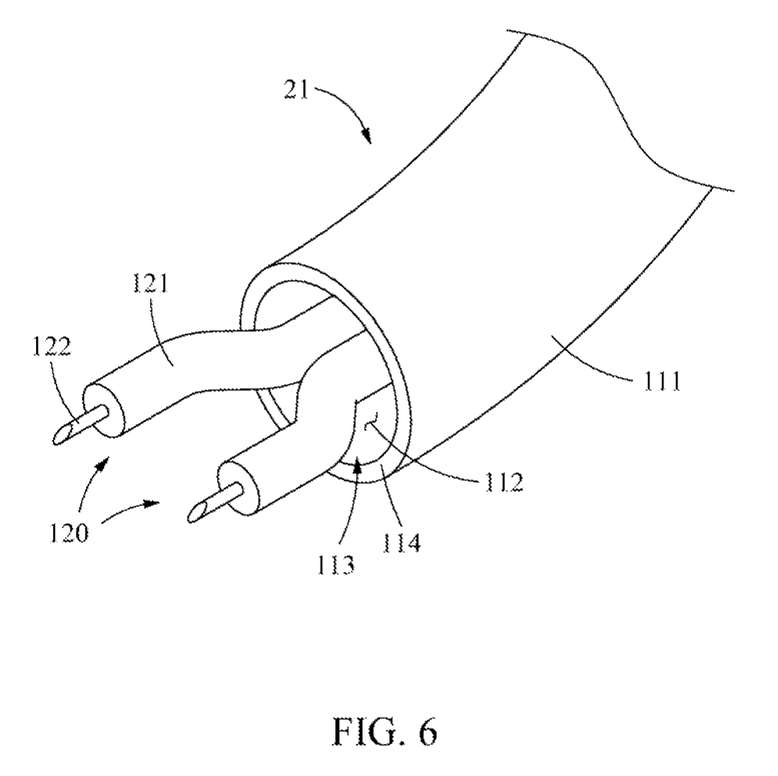
FIG. 6 is a perspective view of a second configuration of an electrical stimulation device of FIG. 4.
Figure 7:
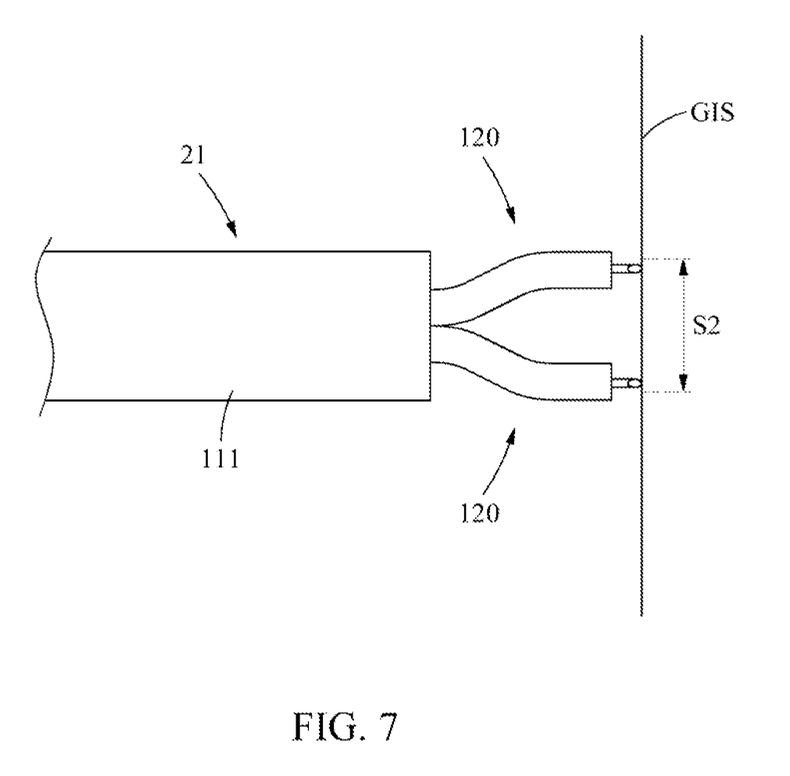
FIG. 7 illustrates a second configuration of a plurality of electrical stimulators of FIG. 4.

FIG. 4 is a perspective view of a first configuration of an electrical stimulation device according to another example embodiment. FIG. 5 illustrates a first configuration of a plurality of electrical stimulators of FIG. 4. FIG. 6 is a perspective view of a second configuration of an electrical stimulation device of FIG. 4. FIG. 7 illustrates a second configuration of a plurality of electrical stimulators of FIG. 4.

Referring to FIGS. 4 through 7, according to another example embodiment, a catheter 21 of an electrical stimulation device may include a plurality of electrical stimulators 120, dissimilar to what has been described above with reference to FIGS. 1 through 3. The electrical stimulators 120 may be controlled by a controller (e.g., the controller 12 of FIG. 1) described above with reference to FIGS. 1 through 3.

The controller may control the electrical stimulators 120 independently for each of them. The independent controlling of the electrical stimulators 120 may include, for example, controlling deployments or withdrawals of respective longitudinal members 121 of the electrical stimulators 120 along the working channel 112, controlling degrees of exposure of the respective longitudinal members 121 and respective tips 122 of the electrical stimulators 120, controlling electrical energy to be applied to the respective tips 122 of the electrical stimulators 120, and controlling an arrangement, an orientation, and an overall shape of the electrical stimulators 120.

The controller may independently control the deployments or withdrawals of the longitudinal members 121 in a longitudinal direction of the working channel 112 such that mutual spaces between the tips 122 of the electrical stimulators 120 are adjusted. For example, the controller may determine the deployments or withdrawals of the longitudinal members 121 such that a mutual space between one pair among the tips 122 increases and a mutual space between another pair among the tips 122 decreases. Accordingly, an overall shape formed by the tips 122 may vary, and a range S1 or S2 in which the tips 122 apply electrical stimulation to a surface GIS of an inner cavity of a target may vary.

The controller may control the electrical stimulators 120, in conjunction with the deployments or withdrawals of the longitudinal members 121, to form a certain shape.

As illustrated in FIGS. 4 and 5, the controller may control the longitudinal members 121 such that the electrical stimulators 120 have a first configuration in which all of at least a portion of the longitudinal members 121 withdraw into the working channel 112 to contract. With the first configuration formed by the electrical stimulators 120, a range of electrical stimulation to be applied to the surface GIS of the inner cavity of the target may be relatively small. As illustrated in FIGS. 6 and 7, the controller may control the longitudinal members 121 such that the electrical stimulators 120 have a second configuration in which all of at least a portion of the longitudinal members 121 deploy outside the working channel 112 to expand. With the second configuration formed by the electrical stimulators 120, a range of electrical stimulation to be applied to the surface GIS of the inner cavity of the target may be relatively great. The controller may control the deployments and withdrawals of the longitudinal members 121 in a combined way such that the electrical stimulators 120 have a shape between the first configuration and the second configuration. Accordingly, a range of electrical stimulation to be applied to the surface of the inner cavity of the target may have a value between S1 and S2.

The controller may control the longitudinal members 121 to deploy in the longitudinal direction of the working channel 112 until all the tips 122 come into contact with the surface of the inner cavity of the target. This may ensure the application of a desired range of electrical stimulation to the surface of the inner cavity of the target.

The controller may independently adjust electrical energy to be applied by the tips 122. For example, the controller may set different potentials to be applied to at least two of the tips 122. When the tips 122 apply electrical stimulation to the surface GIS of the inner cavity of the target, a current flow from one of the tips 122 having a first potential to another one of the tips 122 having a second potential different from the first potential may be induced. This may implement various forms of electrical current flows on the surface GIS of the inner cavity of the target. Similarly, the controller may set different duty cycles, frequencies, currents, and the like of electrical signals to be applied to at least two of the tips 122, thereby implementing various forms of electrical current flows on the surface GIS of the inner cavity of the target to which electrical stimulation is to be applied.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Suitable results may be achieved if the described techniques are performed in a different order, and/or if components in a described system, architecture, device, or circuit are combined in a different manner and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. An electrical stimulation device, comprising:
   an elongated element having a working channel;
   a plurality of electrical stimulators comprising respective longitudinal members each extending in a longitudinal direction of the working channel, and respective tips each provided at a distal end of the longitudinal members and configured to apply electrical stimulation to a target; and
   a controller configured to independently control the electrical stimulators to vary a range of electrical simulation to be applied to the target and to apply a first potential to at least one of the tips and to apply a second potential that is different than the first potential to another one of the tips so that current will flow between the one of the tips having the first potential to the another one of the tips having the second potential.

2. The electrical stimulation device of claim 1, wherein the controller is configured to independently control a deployment or a withdrawal of the longitudinal members in the longitudinal direction of the working channel such that a space between the tips is adjusted.

3. The electrical stimulation device of claim 2, wherein the controller is configured to control the longitudinal members to have a first configuration in which all of at least a portion of the longitudinal members withdraw into the working channel to contract and have a second configuration in which all of at least a portion of the longitudinal members deploy outside the working channel to expand.

4. The electrical stimulation device of claim 2, wherein the controller is configured to control the longitudinal members to deploy in the longitudinal direction of the working channel until all the tips come into contact with a surface of the target.

5. The electrical stimulation device of claim 1, wherein the controller is configured to control a movement of the elongated element along an inner cavity of the target, and control the longitudinal members such that the tips are not exposed to the inner cavity of the target from the working channel during the movement of the elongated element along the inner cavity of the target.

6. The electrical stimulation device of claim 1, wherein the elongated element comprises:
   an opening through which the longitudinal members pass; and
   a closely attached portion configured to surround the opening and configured to be closely attached to a surface of the target.

7. The electrical stimulation device of claim 6, wherein, when the closely attached portion is closely attached to the surface of the target, the controller is configured to suck air into the working channel through the opening.

* * * * *